United States Patent
Keller

(10) Patent No.: US 6,569,203 B1
(45) Date of Patent: May 27, 2003

(54) ALLOPLASTIC REPLACEMENT FOR A LONG BONE

(75) Inventor: Arnold Keller, Kayhude (DE)

(73) Assignee: Waldemar Link (GmbH & Co.), Hamburg (DE)

(*) Notice: Subject to any disclaimer, the term of this patent is extended or adjusted under 35 U.S.C. 154(b) by 195 days.

(21) Appl. No.: 09/651,262

(22) Filed: Aug. 30, 2000

(30) Foreign Application Priority Data

Sep. 24, 1999 (EP) .............................. 99118861

(51) Int. Cl.⁷ .................................. A61F 2/28
(52) U.S. Cl. ................. 623/23.47; 623/23.45; 606/73
(58) Field of Search ............ 623/16.11, 18.11, 623/23.45, 23.47; 606/65, 66, 73; 403/362, 379.3; 411/199, 209, 393, 418; A61F 2/38, 2/30

(56) References Cited

U.S. PATENT DOCUMENTS

| 4,016,874 A | * | 4/1977 | Maffei et al. ................. 606/62 |
| 4,020,929 A | * | 5/1977 | Goldin ........................ 403/362 |
| 4,502,160 A | | 3/1985 | Moore et al. ............ 623/23.45 |
| 5,211,520 A | * | 5/1993 | McKinney ................... 411/418 |
| 5,254,118 A | * | 10/1993 | Mirkovic ................... 606/73 X |
| 5,358,524 A | | 10/1994 | Richelsoph ............... 623/23.47 |
| 5,735,898 A | * | 4/1998 | Branemark ................... 606/73 |

FOREIGN PATENT DOCUMENTS

| EP | 0 212 192 A1 | 3/1987 |
| EP | 0 621 019 A1 | 10/1994 |

OTHER PUBLICATIONS

European Search Report for European Application No. 99118861.6.

* cited by examiner

Primary Examiner—Corrine McDermott
Assistant Examiner—Brian E. Pellegrino
(74) Attorney, Agent, or Firm—Morrison & Foerster LLP

(57) ABSTRACT

Alloplastic replacement for a long bone, in particular for young persons. It comprises a length-adjustable part with a threaded spindle (7), a nut (11) which can be screwed onto the latter, and a sleeve (5) receiving the spindle (7) as far as the nut (11), which are provided with rotation-locking means (9, 12) in connection with a groove (8) included in the threaded spindle (7).

4 Claims, 1 Drawing Sheet

ALLOPLASTIC REPLACEMENT FOR A LONG BONE

FIELD OF THE INVENTION

The invention relates to an alloplastic bone replacement that includes a length-adjustable part having a spindle and a sleeve that are locked against rotation.

BACKGROUND OF THE INVENTION

If a long bone of a young person who has not yet attained his or her full height is completely or partially replaced by an implant, difficulties arise from the fact that the implant is unable to follow the growth of other parts of the body. For example, if the tibia or part thereof is replaced by the implant because of tumour invasion, this implant does not follow the growth of the fibula.

U.S. Pat. No. 5,358,524 discloses a length-adjustable implant in which a threaded spindle is inserted partially in a sleeve and the length of insertion is determined by a nut which can be screwed onto the spindle. By turning the nut, whose axial position relative to the sleeve is fixed, the length of insertion of the spindle can be changed and adapted to the individual requirements. Sleeve and spindle are provided with rotation-locking means comprising a longitudinal groove in the spindle and a pin located on the sleeve and engaging in this longitudinal groove. An axial securing arrangement, i.e. an arrangement preventing an axial relative movement between the spindle and the sleeve in the secured state, is formed by a locking ring arranged on the sleeve for rotationally locking the nut.

The object of the present invention is to simplify the structure of such a bone replacement and make it easier to configure.

SUMMARY OF THE INVENTION

According to the invention, this is achieved by the characterizing clause of claim 1 and preferably by the features of the subclaims. Accordingly, the axial securing arrangement is formed by the bottom of the groove provided for the rotation-locking and by the engagement part engaging in the groove, said engagement part being designed as a screw. The screw thus fulfills two functions: in a first position it engages only loosely in the groove and permits axial movement, whereas in another position it presses on the bottom of the groove and thereby effects the axial securing function. In contrast to the known solution, the locking ring for rotational locking of the nut can be entirely dispensed with. According to the invention, it is also possible to dispense with those components of the known device by means of which the nut is axially fixed relative to the sleeve. Dispensing with these elements results in a considerably simplified construction whose ease of configuration greatly improves its user-friendliness.

The axial fixing can be still further improved by the bottom of the groove having a series of depressions and by the screw engaging in each case in one such depression.

The nut too is preferably provided with rotation-locking means which can likewise be formed by a screw which engages in the longitudinal groove of the spindle.

The arrangement according to the invention is part of an implant which is connected at both ends to parts of the skeleton. For example, a stem for anchoring in the medullary cavity of a bone can be provided at one end or, if desired, at both ends of the arrangement. This stem need not be explained in detail, as stems for anchoring in bone cavities are known. Moreover, a joint component can be provided at one end or, if desired, at both ends, for example a knee joint component at one end and an ankle joint component at the other. In many cases, it will be preferable not to connect these joint components directly and non-releasably to the arrangement, but instead to provide coupling members at the ends of the arrangement on the one hand and on the joint components on the other, thus permitting different combinations. These couplings can be cone couplings, for example, which are known in the prior art.

BRIEF DESCRIPTION OF THE DRAWINGS

The invention is explained in more detail below with reference to the drawing which depicts an advantageous illustrative embodiment, and in which.

DETAILED DESCRIPTION OF THE INVENTION

Figure 1:
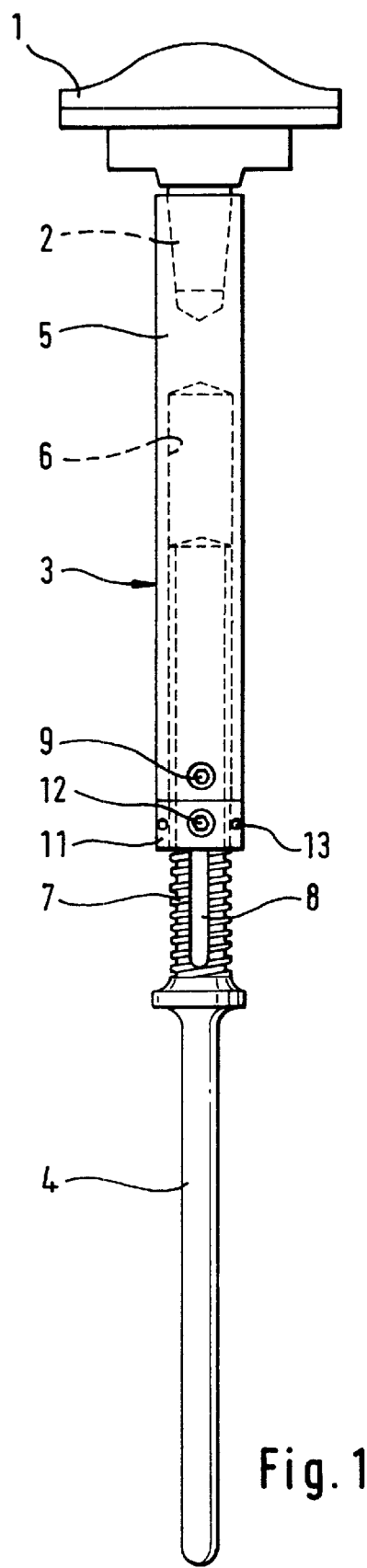
FIG. 1 shows a general view of an implant.
Figure 2:
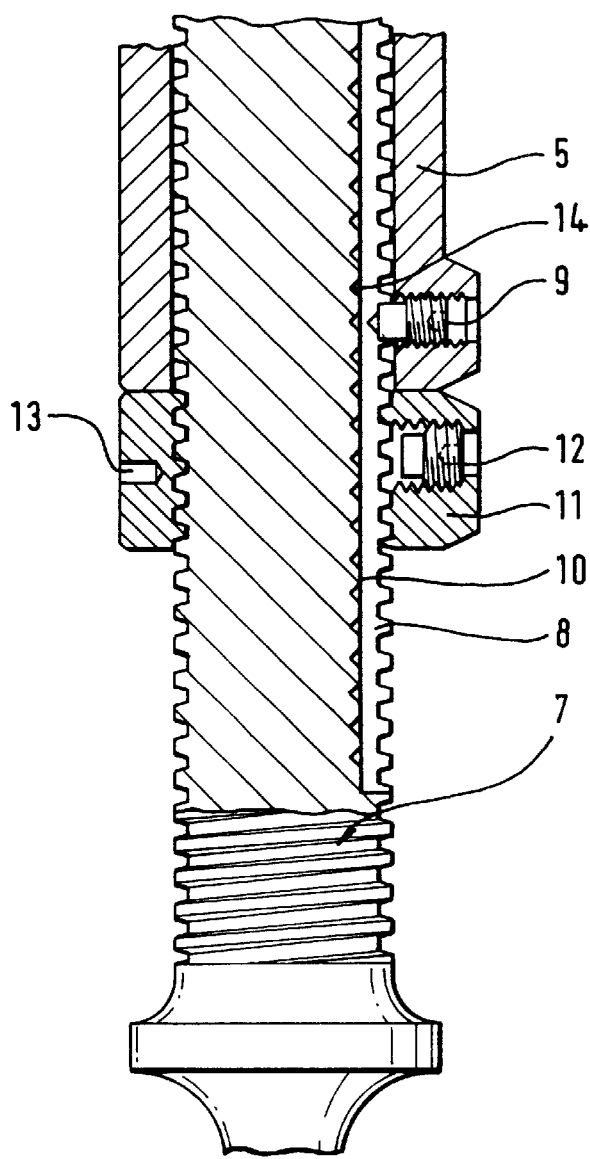
FIG. 2 shows a partial cross section.

A part 3 of adjustable length is connected to the tibial component 1 of a knee prosthesis via a cone coupling 2, and its other end is formed by a stem 4 which is to be anchored in the medullary cavity of the tibia. The implant is intended to replace the upper part of the tibia and the tibial component of the knee joint.

The length-adjustable part 3 of the implant consists of a sleeve 5 which has a cylindrical bore 6. The latter receives the upper section of a threaded spindle 7 without any substantial radial play and so that the latter is freely movable in the longitudinal direction. The threaded spindle 7 comprises a longitudinal groove 8. At the lower end, i.e. at the end of the sleeve 5 remote from the coupling 2, the sleeve 5 comprises a radial threaded bore which receives a securing screw 9 engaging in the groove 8. As long as it does not press against the bottom 10 of the groove, the spindle 7 is freely displaceable in the sleeve 5 in the longitudinal direction, but not rotatable.

Sitting on the threaded spindle 7 there is a nut 11 with a securing screw 12 whose configuration is identical to that of the securing screw 9. When it is in engagement in the groove 8, the nut cannot rotate relative to the threaded spindle. If one wishes to turn the nut 11, the screw 12 is withdrawn from the groove The nut 11 has a number of bores 13 distributed around its entire circumference, it being possible for a pin to be inserted into the bores 13 in order to turn the nut. When adjusting the length of the implant, the nut 11 is always set in such a way that its securing screw 12 can engage in the groove 8. This means that the nut 11 on the threaded spindle 7 can assume axial positions which differ from each other by one pitch. This also gives the sleeve 5, whose lower end rests on the nut 11, discrete positions relative to the threaded spindle 7, which positions differ from each other by one pitch. At each location where the tip of the securing screw 9 is situated in these respective positions, the bottom 10 of the groove has depressions 14 which are spaced apart from each other by one thread pitch. The securing screw 9 therefore secures the respective chosen positions of the sleeve not only by frictional force on the bottom 10 of the groove, but also by positive engagement in the depressions 14.

When adjusting the length, the operating surgeon proceeds in the manner set out below in order to effect lengthening, after first making an incision into the covering tissue to gain access to the nut 11 and the securing screw 9.

The securing screw 9 is loosened so that it is freed from the bottom 10 of the groove and the depressions 14 formed in the latter, but is still located in the groove 8. The securing screw 12 in the nut 11 is loosened and withdrawn from the groove 8 so that the nut 11 can be freely rotated. It is then turned in steps, by engaging the pin in the bores 13, until the desired adjustment is obtained, in which the securing screw 12 is once again positioned over the groove 8. In this position, the securing screws 9 and 12 are once again tightened, by which means the adjustment is secured.

What is claimed is:

1. Alloplastic replacement for a long bone, comprising:
    a length-adjustable part having a threaded spindle and comprising, at least at one end, a stem for anchoring the replacement in a medullary canal,
    a nut adapted to be screwed onto the spindle,
    a sleeve adapted for receiving the spindle as far as the nut screwed onto the spindle,
    the spindle and the sleeve have a rotation-locking arrangement comprising a longitudinal groove in the spindle and an engagement part in the form of a screw located on the sleeve and adapted for engaging in the longitudinal groove, and
    an axial securing arrangement formed by the bottom of the groove and the engagement part,
    wherein the bottom of the groove has depressions for positive engagement of the screw; and
    wherein the depressions are spaced apart from each other by one thread pitch.

2. Bone replacement according to claim 1, wherein the nut is also provided with a rotation-locking arrangement.

3. Bone replacement according to claim 2, wherein, at least at one end, the bone replacement is connected to a joint prosthesis or comprises a coupling element.

4. Bone replacement according to claim 1, wherein, at least at one end, the bone replacement is connected to a joint prosthesis or comprises a coupling element.

* * * * *